United States Patent
Abhyankar

(10) Patent No.: US 12,391,760 B2
(45) Date of Patent: Aug. 19, 2025

(54) METHOD OF TREATING PRIMARY SCLEROSING CHOLANGITIS

(71) Applicant: Takeda Pharmaceutical Company Limited, Osaka (JP)

(72) Inventor: Brihad Abhyankar, Watford (GB)

(73) Assignee: Takeda Pharmaceutical Company Limited, Osaka (JP)

( * ) Notice: Subject to any disclaimer, the term of this patent is extended or adjusted under 35 U.S.C. 154(b) by 160 days.

(21) Appl. No.: 17/184,116

(22) Filed: Feb. 24, 2021

(65) Prior Publication Data

US 2021/0388092 A1    Dec. 16, 2021

Related U.S. Application Data

(63) Continuation of application No. 15/556,186, filed as application No. PCT/US2016/020819 on Mar. 4, 2016, now abandoned.

(60) Provisional application No. 62/129,698, filed on Mar. 6, 2015.

(51) Int. Cl.
| | |
|---|---|
| *A61K 39/395* | (2006.01) |
| *A61K 39/00* | (2006.01) |
| *C07K 16/28* | (2006.01) |

(52) U.S. Cl.
CPC .... *C07K 16/2839* (2013.01); *A61K 39/39533* (2013.01); *A61K 2039/505* (2013.01); *A61K 2039/54* (2013.01); *A61K 2039/545* (2013.01); *C07K 2317/24* (2013.01); *C07K 2317/76* (2013.01)

(58) Field of Classification Search
None
See application file for complete search history.

(56) References Cited

U.S. PATENT DOCUMENTS

| | | |
|---|---|---|
| 7,090,845 B2 | 8/2006 | Fong et al. |
| 9,663,579 B2 | 5/2017 | Fox et al. |
| 9,764,033 B2 | 9/2017 | Diluzio et al. |
| 10,004,808 B2 | 6/2018 | Fox et al. |
| 10,040,855 B2 | 8/2018 | Diluzio et al. |
| 10,143,752 B2 | 12/2018 | Fox et al. |
| 11,560,434 B2 | 1/2023 | Diluzio et al. |
| 2012/0282249 A1 | 11/2012 | Fox et al. |
| 2018/0051086 A1 | 2/2018 | Abhyankar |
| 2018/0207279 A1 | 7/2018 | Fox et al. |
| 2018/0289811 A1 | 10/2018 | Fox et al. |
| 2018/0327497 A1 | 11/2018 | Diluzio et al. |
| 2018/0346578 A1 | 12/2018 | Diluzio et al. |
| 2019/0076532 A1 | 3/2019 | Diluzio et al. |
| 2019/0231878 A1 | 8/2019 | Brown et al. |
| 2020/0206353 A1 | 7/2020 | Fox et al. |
| 2021/0052733 A1 | 2/2021 | Diluzio et al. |
| 2021/0340261 A1 | 11/2021 | Diluzio et al. |
| 2022/0370617 A1 | 11/2022 | Diluzio et al. |

FOREIGN PATENT DOCUMENTS

| | | |
|---|---|---|
| WO | 9958573 A1 | 11/1999 |
| WO | 2007061679 A1 | 5/2007 |
| WO | 2012151248 A2 | 11/2012 |

OTHER PUBLICATIONS

Laborda et al. Vedolizumab Therapy in Children With Primary Sclerosing Cholangitis: Data From the Pediatric Primary Sclerosing Cholangitis Consortium. JPGN 2020;71: 459-464. (Year: 2020).*
Stanich et al. Alkaline phosphatase normalization is associated with better prognosis in primary sclerosing cholangitis. Dig Liver Dis. Apr. 2011; 43(4): 309-313. (Year: 2011).*
Jazrawi et al. Kinetics of Hepatic Bile Acid Handling in Cholestatic Liver Disease: Effect of Ursodeoxycholic Acid. Gastroenterology 1994; 106:134-142. (Year: 1994).*
Beuers et al. Ursodeoxycholic acid for treatment of primary sclerosing cholangitis: a placebo-controlled trial. Hepatology. Sep. 1992; 16(3):707-14. (Year: 1992).*
Stanich et al. Alkaline phosphatase normalization is associated with better prognosis in primary sclerosing cholangitis. Digestive and Liver Disease. 43(4):309-313, 2011. (Year: 2011).*
Caron et al. Vedolizumab for primary sclerosing cholangitis associated with inflammatory bowel disease: A multicentre cohort study fromt he GETAID. Journal of Crohn's and Colitis, (Feb. 2018) vol. 12, Supp. Supplement 1, pp. S278. Abstract No. P347. (Year: 2018).*
Williamson et al. Clinical and translational outcomes in patients with primary sclerosing cholangitis and inflammatory bowel disease receiving vedolizumab. Gastroenterology, (Apr. 2017) vol. 152, No. 5, Suppl. 1, pp. S1186-S1187. (Year: 2017).*
International Search Report and Written Opinion mailed Jun. 15, 2016 in PCT Application No. PCT/US/2016/020819 (3 pages).
Ahmad H Ali et al: "Current research on the treatment of primary sclerosing cholangitis", Intractable & Rare Disease Research, vol. 4, No. 1, Jan. 1, 2015, pp. 1-6, www.irdrjournal.com.
C.S. Tse et al: "Effects of vedolizumab, adalimumab and infliximab on biliary inflammation in individuals with primary sclerosing cholangitis and inflammatory bowel disease", Alimentary Pharmacology & Therapeutics., vol. 48, No. 2, May 28, 2018,, pp. 190-195.
"7 Westferry Circus; Canary Wharf; London E14 4HB; United Kingdom and Agency of the European Union EPAR Summary for the public" Jun. 1, 2014. Retrieved from the internet: http:// www.ema.europa.eu/docs/human/02782/WC500168532.pdf.
Krijger et al., Return to sender: Lymphocyte trafficking mechanisms as contributors to primary sclerosing cholangitis, Journal of Hepatology 2019, vol. 71, pp. 603-615.

(Continued)

*Primary Examiner* — Maher M Haddad
(74) *Attorney, Agent, or Firm* — Womble Bond Dickinson (US) LLP

(57) ABSTRACT

Disclosed is a method for treating a subject having primary sclerosing cholangitis, comprising administering to said subject an effective amount of a humanized antibody or antigen-binding fragment thereof having binding specificity for α4β7 integrin.

10 Claims, No Drawings
Specification includes a Sequence Listing.

(56) References Cited

OTHER PUBLICATIONS

Ma and Kotze, "Editorial: biologic therapies for primary sclerosing cholangitis—more disappointment than promise?" AP&T Alimentary Pharmacol. & Therapeut. (2018): 576-577. DOI: 10.1111/apl.14858.

Westerveld et al. Vedolizumab: a novel medical intervention in the treatment of primary sclerosing cholangitis BMJ Case Rep. (2017). DOI:10.1136/bcr-2017-220351.

Lynch et al. Effects of Vedolizumab in Patients with Primary Sclerosing Cholangitis and Inflammatory Bowel Diseases. Clinical Gastroenterology and Hepatology. pp. 1-15, https://doi.org/10.1016/j.cgh.2019.05.013. Available on line May 13, 2019 (Year: 2019).

Christensen et al. Vedolizumab in patients with concurrent primary sclerosing cholangitis and inflammatory bowel disease does not improve liver biochemistry but is safe and effective for the bowel disease. Aliment Pharmacol Ther. 2018;47:753-762. (Year: 2018).

Doherty et al. Vedolizumab: Effects on liver function in an IBDand IBD/PSC cohort. Clinical: Therapy and observation, 2018, P582 ( Year: 2018).

Raine T. Vedolizumab for inflammatory bowel disease: Changing the game, or more of the same? United European Gastroenterol J . Oct. 2014;2(5):333-44. (Year: 2014).

Bowlus, Christopher, alpha4Beta7-Integrin Ligand Development for the Treatment of PSC. PSC Partners Seeking a Cure Research Grants—PSC Partners Seeking a Cure. Grant proposal Granted 2009. p. 1 (Year: 2009).

Adams and Eksteen. Aberrant homing of mucosal T cells and extra-intestinal manifestations of inflammatory bowel disease. Nature Reviews Immunologyvolume 6, pp. 244-251 (2006) (Year: 2006).

Workshop—The Primary Sclerosing Cholangitis/Inflammatory Bowel Disease Link: An informative and interactive workshop for medical professionals and Patients. University of Colorado, Denver, Oct. 3, 2009. (Year: 2009).

Rietdijk et al. Vedolizumab for the treatment of ulcerative colitis Expert Rev. Clin. Pharmacol. 7(4), 423-430 (2014), published online May 6, 2014. (Year: 2014).

Pollheimer et al. Pathogenesis of primary sclerosing cholangitis. Best Pract Res Clin Gastroenterol. Dec. 2011; 25(6): 727-739. ( Year: 2011).

Mamari et al. Improvement of serum alkaline phosphatase to <1.5 upper limit of normal predicts better outcome and reduced risk of cholangiocarcinoma in primary sclerosing cholangitis. Journal of Hepatology 2013 vol. 58 j 329-334. (Year: 2013).

Rupp et al. Reduction in alkaline phosphatase is associated with longer survival in primary sclerosing cholangitis, independent of dominant stenosis. Aliment Pharmacol Ther 2014;40: 1292-1301. (Year: 2014).

Villanacci et al. Histological healing in inflammatory bowel disease: A still unfulfilled promise. World J Gastroenterol Feb. 21, 2013; 19(7): 968-978 (Year: 2013).

Caron et al. Vedolizumab Therapy is Ineffective for Primary Sclerosing Cholangitis in Patients With Inflammatory Bowel Disease: A Get Aid Multicentre Cohort Study. Journal of Crohn's and Colitis, 2019, 1239-1247. (Year: 2019).

Lynch et al. Effects of Vedolizumab in Patients With Primary Sclerosing Cholangitis and Inflammatory Bowel Diseases. Clinical Gastroenterology and Hepatology 2020;18:179-187. (Year: 2020).

Vuppalanchi et al. Magic Wand and Crystal Ball for Primary Sclerosing Cholangitis Gastroenterology. Apr. 2014; 146(4) :890-2. (Year: 2014).

Corpechot et al. Baseline Values and Changes in Liver Stiffness Measured by Transient Elastography Are Associated With Severity of Fibrosis and Outcomes of Patients With Primary Sclerosing Cholangitis. Gastroenterology. Apr. 2014;146:970-979. (Year: 2014).

ClinicalTrials.gov [Internet]. Efficacy and Safety of Vedolizumab Intravenous (IV) in the Treatment of Primary Sclerosing Cholangitis in Subjects With Underlying Inflammatory Bowel Disease, NCT03035058, Mar. 7, 2017. Available from: https://clinicaltrials.gov/study/NCT03035058.

* cited by examiner

SEQUENCE LISTING

<160> NUMBER OF SEQ ID NOS: 15

<210> SEQ ID NO 1
<211> LENGTH: 1445
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
gaattctcga gatcgatctc accatgggat ggagctgtat catcctcttc ttggtagcaa     60
cagctacagg tgtccactcc caggtgcaat tggtgcagtc tggggctgag gttaagaagc    120
ctggggcttc agtgaaggtg tcctgcaagg gttctggcta caccttcacc agctactgga    180
tgcattgggt gaggcaggcg cctggccaac gtctagagtg gatcggagag attgatcctt    240
ctgagagtaa tactaactac aatcaaaaat tcaagggacg cgtcacattg actgtagaca    300
tttccgctag cacagcctac atggagctct ccagcctgag atctgaggac actgcggtct    360
actattgtgc aagagggggt tacgacggat gggactatgc tattgactac tggggtcaag    420
gcaccctggt caccgtcagc tcagcctcca ccaagggccc atcggtcttc cccctggcac    480
cctcctccaa gagcacctct ggggcacag cggccctggg ctgcctggtc aaggactact    540
tccccgaacc ggtgacggtg tcgtggaact caggcgccct gaccagcggc gtgcacacct    600
tcccggctgt cctacagtcc tcaggactct actccctcag cagcgtggtg accgtgccct    660
ccagcagctt gggcacccag acctacatct gcaacgtgaa tcacaagccc agcaacacca    720
aggtggacaa gaaagttgag cccaaatctt gtgacaaaac tcacacatgc ccaccgtgcc    780
cagcacctga actcgcgggg gcaccgtcag tcttcctctt ccccccaaaa cccaaggaca    840
ccctcatgat ctcccggacc cctgaggtca catgcgtggt ggtggacgtg agccacgaag    900
accctgaggt caagttcaac tggtacgtgg acggcgtgga ggtgcataat gccaagacaa    960
agccgcggga ggagcagtac aacagcacgt accgtgtggt cagcgtcctc accgtcctgc   1020
accaggactg gctgaatggc aaggagtaca agtgcaaggt ctccaacaaa gccctcccag   1080
cccccatcga gaaaaccatc tccaaagcca aagggcagcc ccgagaacca caggtgtaca   1140
ccctgccccc atcccgggat gagctgacca agaaccaggt cagcctgacc tgcctggtca   1200
aaggcttcta tcccagcgac atcgccgtgg agtgggagag caatgggcag ccggagaaca   1260
actacaagac cacgcctccc gtgctggact ccgacggctc cttcttcctc tacagcaagc   1320
tcaccgtgga caagagcagg tggcagcagg ggaacgtctt ctcatgctcc gtgatgcatg   1380
aggctctgca caaccactac acgcagaaga gcctctccct gtctccgggt aaataatcta   1440
gagca                                                              1445
```

<210> SEQ ID NO 2
<211> LENGTH: 470
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Met Gly Trp Ser Cys Ile Ile Leu Phe Leu Val Ala Thr Ala Thr Gly
1               5                  10                  15

Val His Ser Gln Val Gln Leu Val Gln Ser Gly Ala Glu Val Lys Lys
            20                  25                  30
```

-continued

Pro Gly Ala Ser Val Lys Val Ser Cys Lys Gly Ser Gly Tyr Thr Phe
            35                  40                  45

Thr Ser Tyr Trp Met His Trp Val Arg Gln Ala Pro Gly Gln Arg Leu
    50                  55                  60

Glu Trp Ile Gly Glu Ile Asp Pro Ser Glu Ser Asn Thr Asn Tyr Asn
65                  70                  75                  80

Gln Lys Phe Lys Gly Arg Val Thr Leu Thr Val Asp Ile Ser Ala Ser
                85                  90                  95

Thr Ala Tyr Met Glu Leu Ser Ser Leu Arg Ser Glu Asp Thr Ala Val
                100                 105                 110

Tyr Tyr Cys Ala Arg Gly Gly Tyr Asp Gly Trp Asp Tyr Ala Ile Asp
            115                 120                 125

Tyr Trp Gly Gln Gly Thr Leu Val Thr Val Ser Ser Ala Ser Thr Lys
        130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Ile Cys Asn
        210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Ala Gly Ala Pro Ser Val Phe Leu Phe Pro Pro Lys Pro Lys Asp
                260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
        290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 3
<211> LENGTH: 751
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gaattctcga gatcgatctc accatgggat ggagctgtat catcctcttc ttggtagcaa      60
cagctacagg tgtccactcc gatgtagtga tgactcaaag tccactctcc ctgcctgtca     120
cccctggaga accagcttct atctcttgca ggtctagtca gagtcttgca aagagttatg     180
ggaacaccta tttgtcttgg tacctgcaga agcctggcca gtctccacag ctcctcatct     240
atgggatttc aacagatttt ctggggtgc cagacaggtt cagtggcagt ggttcaggga     300
cagatttcac actcaagatc tcgcgagtag aggctgagga cgtgggagtg tattactgct     360
tacaaggtac acatcagccg tacacgttcg gacagggac caaggtggag atcaagcgta     420
cggtggctgc accatctgtc ttcatcttcc cgccatctga tgagcagttg aaatctggaa     480
ctgcctctgt tgtgtgcctg ctgaataact tctatcccag agaggccaaa gtacagtgga     540
aggtggataa cgcccctcca atcgggtaact cccaggagag tgtcacagag caggacagca     600
aggacagcac ctacagcctc agcagcaccc tgaccctgag caaagcagac tacgagaaac     660
acaaagtcta cgcctgcgaa gtcacccatc agggcctgag ctcgcccgtc acaaagagct     720
tcaacagggg agagtgttag tctagagcag c                                    751

<210> SEQ ID NO 4
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Gly Trp Ser Cys Ile Ile Leu Phe Leu Val Ala Thr Ala Thr Gly
1               5                   10                  15

Val His Ser Asp Val Val Met Thr Gln Ser Pro Leu Ser Leu Pro Val
            20                  25                  30

Thr Pro Gly Glu Pro Ala Ser Ile Ser Cys Arg Ser Ser Gln Ser Leu
        35                  40                  45

Ala Lys Ser Tyr Gly Asn Thr Tyr Leu Ser Trp Tyr Leu Gln Lys Pro
    50                  55                  60

Gly Gln Ser Pro Gln Leu Leu Ile Tyr Gly Ile Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Leu Gln Gly Thr His Gln Pro Tyr Thr Phe Gly Gln Gly Thr Lys Val
        115                 120                 125

Glu Ile Lys Arg Thr Val Ala Ala Pro Ser Val Phe Ile Phe Pro Pro

```
                130                 135                 140
Ser Asp Glu Gln Leu Lys Ser Gly Thr Ala Ser Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
        210                 215                 220

Leu Ser Ser Pro Val Thr Lys Ser Phe Asn Arg Gly Glu Cys
225                 230                 235

<210> SEQ ID NO 5
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Ala Lys Ser
            20                  25                  30

Tyr Gly Asn Thr Tyr Leu Ser Trp Tyr Leu Gln Lys Pro Gly Gln Ser
        35                  40                  45

Pro Gln Leu Leu Ile Tyr Gly Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Gly
                85                  90                  95

Thr His Gln Pro Tyr Thr Phe Gly Gln Gly Thr Lys Val Glu Ile Lys
            100                 105                 110

Arg Ala Asp Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 6
<211> LENGTH: 107
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 6

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 7
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 7

```
Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105
```

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 8

```
Ser Tyr Trp Met His
1               5
```

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic

```
                           peptide

<400> SEQUENCE: 9

Glu Ile Asp Pro Ser Glu Ser Asn Thr Asn Tyr Asn Gln Lys Phe Lys
1               5                   10                  15

Gly

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Gly Tyr Asp Gly Trp Asp Tyr Ala Ile Asp Tyr
1               5                   10

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Ser Ser Gln Ser Leu Ala Lys Ser Tyr Gly Asn Thr Tyr Leu Ser
1               5                   10                  15

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Ile Ser Asn Arg Phe Ser
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Gln Gly Thr His Gln Pro Tyr Thr
1               5

<210> SEQ ID NO 14
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Val Met Thr Gln Ser Pro Leu Ser Leu Pro Val Thr Pro Gly
1               5                   10                  15
```

```
Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
            85                  90                  95

Leu Gln Thr Pro Gln Thr Phe Gly Gln Gly Lys Val Glu Ile Lys
            100                 105                 110

<210> SEQ ID NO 15
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
            50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Gly Gly Tyr Tyr Gly Ser Gly Ser Asn Tyr Trp Gly Gln Gly
            100                 105                 110

Thr Leu Val Thr Val Ser Ser
            115
```

METHOD OF TREATING PRIMARY SCLEROSING CHOLANGITIS

RELATED APPLICATIONS

This application is a continuation of U.S. Non-Provisional application Ser. No. 15/556,186, filed on Sep. 6, 2017, which is a U.S. National Phase Application under 35 U.S.C. § 371 of International Application No. PCT/US2016/020819, filed on Mar. 4, 2016, which claims the benefit of U.S. Provisional Application No. 62/129,698, filed on Mar. 6, 2015. The entire contents of the foregoing applications are hereby incorporated by reference.

SEQUENCE LISTING

The instant application contains a Sequence Listing which has been submitted in ASCII format via EFS-Web and is hereby incorporated by reference in its entirety. Said ASCII copy, created on Mar. 25, 2021, is named T103022_1170US_C1_(0463_4)_SL and is 17,854 bytes in size.

BACKGROUND

Vedolizumab and other agents that bind α4 integrin, as well as TNF inhibitors, have been used to treat inflammatory bowel diseases, but these agents have not been used to treat sclerotic diseases of the liver, such as primary sclerosing cholangitis (PSC).

PSC is a chronic cholestatic hepatobiliary disease characterized by inflammation and progressive fibrosis of intra- and extra-hepatic bile ducts leading to biliary cirrhosis, portal hypertension, and finally liver failure. As with many chronic liver diseases, PSC progresses insidiously even in asymptomatic patients. There is currently no effective treatment and therapy options are limited to managing complications: e.g., dilatation of dominant strictures and early diagnosis of cholangiocarcinoma. Orthotopic liver transplantation is currently the only life-extending therapy for patients progressing to liver failure.

PSC is a disease of relatively young people, with a median age at diagnosis of 40 years. PSC has a profound impact on patients and is accompanied by substantial longstanding morbidity, before liver transplantation or death ensues. Overall PSC is relatively uncommon (annual incidence of 1:100,000), however, the natural history of the disease and mean survival rates (~12 years from diagnosis) ensure that disease prevalence approaches 8-14 in 100,000.

PSC has an unknown etiology, however one hypothesis suggests that it is immune-mediated, resulting in an erroneous chronic inflammatory response against the biliary epithelium. About 70% to 80% of PSC patients also suffer from inflammatory bowel disease (IBD), such as ulcerative colitis (UC), Crohn's disease (CD), and IBD Unclassified (IBDU). Patients suffering from both PSC and IBD are viewed as distinct from a number of other minor PSC subtypes, e.g., immunoglobulin G4 (IgG4)-positive sclerosing cholangitis; PSC with autoimmune hepatitis; small-duct associated PSC.

PSC represents a disease of very high unmet medical need, which despite numerous studies with various agents (Karlsen et al., *Aliment. Pharmacol. Ther.* 39:282-301 (2014)), has no therapy shown to prevent disease progression. Treatment options are limited to attempting to manage ongoing symptoms and complications. This places patients with PSC at risk from liver failure and ultimately death, with only liver transplantation as a potential option. Thus, a need exists for improved therapeutic approaches to primary sclerosing cholangitis.

SUMMARY

In a first aspect, the invention relates to a method for treating a human subject suffering from primary sclerosing cholangitis (PSC), comprising the steps of: administering to a subject suffering from PSC, an effective amount of an anti-α4β7 antibody, wherein the anti-α4β7 antibody has binding specificity for the α4β7 complex, and wherein the antigen-binding region comprises the CDRs: light chain: CDR1 SEQ ID NO:11, CDR2 SEQ ID NO:12, CDR3 SEQ ID NO:13; heavy chain: CDR1 SEQ ID NO:8, CDR2 SEQ ID NO:9, and CDR3 SEQ ID NO:10.

In some embodiments, an effective amount is an amount sufficient to normalize serum alkaline phosphatase (ALP) of the subject. In some embodiments, an effective amount is an amount sufficient to reduce serum alkaline phosphatase (ALP) of the subject by at least 35%. In some embodiments, an effective amount is an amount sufficient to improve Ishak necroinflammatory grading score by at least one point.

In some embodiments, the anti-α4β7 antibody may be administered to the subject according to the following dosing regimen: (a) an initial dose of 300 mg of the anti-α4β7 antibody as an intravenous infusion; (b) followed by a second subsequent dose of 300 mg of the anti-α4β7 antibody as an intravenous infusion at about two weeks after the initial dose; (c) followed by a third subsequent dose of 300 mg of the anti-α4β7 antibody as an intravenous infusion at about six weeks after the initial dose; (d) followed by a fourth and subsequent doses of 300 mg of the anti-α4β7 antibody as an intravenous infusion every four weeks or every eight weeks after the third subsequent dose of the anti-α4β7 antibody as needed.

In some embodiments, the subject has chronic cholestatic liver disease with a subsequent diagnosis of PSC based on cholangiographic findings of intrahepatic and/or extrahepatic bile duct irregularities consistent with PSC.

In some embodiments, the subject further has diagnosis of IBD by clinical and endoscopic evidence and corroborated by a histopathology report. In some embodiments, the subject does not have a diagnosis of IBD.

In some embodiments, the subject has alkaline phosphatase (ALP) elevation to at least 1.6 times the upper limit of normal (ULN) at the time of initial treatment.

In some embodiments, the subject's Ishak fibrosis staging score is improved, maintained or normalized.

In some embodiments, the subject's Amsterdam Cholestatic Complaints (ACCS) has improved, maintained or normalized, 5-D itch scale has improved, maintained or normalized, or the subject has a liver stiffness TE score of less than or equal to 14.3 kPa, as assessed by Vibration Controlled Transient Elastography.

In some embodiments, the anti-α4β7 antibody is administered to the subject intravenously. In other embodiments, the anti-α4β7 antibody is administered subcutaneously. In some embodiments, the anti-α4β7 antibody is administered intravenously during part of the therapeutic regimen and subcutaneously during part of the therapeutic regimen.

In some embodiments, a PSC-related outcome selected from the group consisting of progression to cirrhosis, liver failure, death and liver transplantation is delayed or prevented. In some embodiments, a PSC-related complication selected from the group consisting of ascites, hepatic encephalopathy, development of varices, jaundice, variceal bleeding, cholangiocarcinoma, hepatocellular carcinoma, evidence of cirrhosis, and colorectal cancer is delayed or prevented.

In some embodiments, the treatment does not cause one or more than one adverse event selected from the group consisting of hepatoxicity, PML, cholangiocarcinoma, one or more complications due to portal hypertension, leucopenia, lymphopenia, colorectal cancer, infusion-related reactions, infection, acute respiratory failure, acute respiratory distress syndrome, Torsade de pointes, ventricular fibrillation, ventricular tachycardia, malignant hypertension, convulsive seizure, agranulocytosis, aplastic anemia, toxic epidermal necrolysis, Stevens-Johnson syndrome, hepatic necrosis, acute liver failure, anaphylactic shock, acute renal failure, pulmonary hypertension, pulmonary fibrosis, confirmed or suspected endotoxin shock, confirmed or suspected transmission of infectious agent by a medicinal product, neuroleptic malignant syndrome, malignant hyperthermia, spontaneous abortion, stillbirth, and fetal death.

In some embodiments, the anti-α4β7 antibody has a heavy chain variable region sequence comprising amino acid residues 20 to 140 of SEQ ID NO:2, and a light chain variable region comprising amino acids 20 to 131 of SEQ ID NO:4 or amino acids 21 to 132 of SEQ ID NO:5. In some embodiments, the anti-α4β7 antibody is vedolizumab.

In another aspect, the invention relates to a pharmaceutical composition comprising an antibody having binding specificity for human α4β7 integrin for the manufacture of a medicament for treating primary sclerosing cholangitis.

In another aspect, the invention relates to a pharmaceutical composition comprising an antibody having binding specificity for human α4β7 integrin for use in treating primary sclerosing cholangitis.

In some embodiments, the pharmaceutical composition may be formulated as a lyophilized preparation. In some embodiments, the pharmaceutical may be formulated as a liquid preparation.

In some embodiments, the pharmaceutical composition may be formulated in a device for subcutaneous administration.

In another aspect, the invention relates to a therapeutically effective amount of an anti-α4β7 antibody for use in the treatment or prophylaxis of PSC in an individual in need thereof.

In another aspect, the invention relates to use of a therapeutically effective amount of an anti-α4β7 antibody for the manufacture of a medicament for use in the treatment or prophylaxis of PSC in a subject in need thereof.

In some embodiments, the anti-α4β7 antibody is humanized.

DETAILED DESCRIPTION

The invention relates to methods of treating primary sclerosing cholangitis (PSC) by administering an anti-α4β7 antibody. PSC is distinguished from secondary sclerosing cholangitis (SSC). Patients suffering from PSC at first can be asymptomatic, with no physical abnormalities, but over time, death results from cancer or liver failure, unless the patient undergoes liver transplantation. Patients suffering from PSC additionally can be suffering from IBD. "PSC with underlying IBD" is a term which indicates a diagnosis comprising both conditions, but does not indicate IBD as the cause of PSC or IBD as a necessary association with PSC.

The methods and compositions related to treatment with an anti-α4β7 antibody can improve the outcome for PSC patients.

Definitions

The term "pharmaceutical formulation" refers to a preparation that contains an anti-α4β7 antibody in such form as to permit the biological activity of the antibody to be effective, and which contains no additional components which are unacceptably toxic to a subject to which the formulation would be administered.

The cell surface molecule, "α4β7 integrin," or "α4β7," is a heterodimer of an $\alpha_4$ chain (CD49D, ITGA4) and a $\beta_7$ chain (ITGB7). Each chain can form a heterodimer with an alternative integrin chain, to form $\alpha_4\beta_1$ or $\alpha_E\beta_7$. Human $\alpha_4$ and $\beta_7$ genes (GenBank (National Center for Biotechnology Information, Bethesda, MD) RefSeq Accession numbers NM_000885 and NM_000889, respectively) are expressed by B and T lymphocytes, particularly memory CD4+ lymphocytes. Typical of many integrins, α4β7 can exist in either a resting or activated state. Ligands for α4β7 include vascular cell adhesion molecule (VCAM), fibronectin and mucosal addressin (MAdCAM (e.g., MAdCAM-1)).

As used herein, a human antibody or antigen-binding fragment thereof that has "binding specificity for the α4β7 complex" binds to α4β7, but not to α4β1 or αEβ7.

The term "antibody" herein is used in the broadest sense and specifically covers full length monoclonal antibodies, immunoglobulins, polyclonal antibodies, multispecific antibodies (e.g. bispecific antibodies) formed from at least two full length antibodies, e.g., each to a different antigen or epitope, and individual antigen binding fragments, including dAbs, scFv, Fab, F(ab)'$_2$, Fab', including human, humanized and antibodies from non-human species and recombinant antigen binding forms such as monobodies and diabodies.

The term "human antibody" includes an antibody that possesses a sequence that is derived from a human germ-line immunoglobulin sequence, such as an antibody derived from transgenic mice having human immunoglobulin genes (e.g., XENOMOUSE genetically engineered mice (Abgenix, Fremont, CA), HUMAB-MOUSE®, KIRIN TC MOUSE™ transchromosome mice, KMMOUSE® (MEDAREX, Princeton, NJ)), human phage display libraries, human myeloma cells, or human B cells.

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816, 567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA*, 81:6851-6855 (1984)). Chimeric antibodies of interest herein include "primatized" antibodies comprising variable domain antigen binding sequences derived from a non-human primate (e.g. Old World Monkey, Ape etc) and human constant region sequences.

"Antigen binding fragments" of the e.g., humanized, antibody prepared in the formulation, use and/or method of the invention comprise at least the variable regions of the heavy and/or light chains of an anti-α4β7 antibody. For example, an antigen binding fragment of vedolizumab comprises amino acid residues 20-131 of the humanized light chain sequence of SEQ ID NO:4. Examples of such antigen binding fragments include Fab fragments, Fab' fragments, scFv and F(ab')$_2$ fragments of an antibody known in the art. Antigen binding fragments of the anti-α4β7 antibody of the invention can be produced by enzymatic cleavage or by recombinant techniques. For instance, papain or pepsin cleavage can be used to generate Fab or F(ab')$_2$ fragments, respectively. Antibodies can also be produced in a variety of truncated forms using antibody genes in which one or more stop codons have been introduced upstream of the natural stop site. For example, a recombinant construct encoding the heavy chain of an F(ab')$_2$ fragment can be designed to include DNA sequences encoding the $CH_I$ domain and hinge region of the heavy chain. In one aspect, antigen binding fragments inhibit binding of α4β7 integrin to one or more of its ligands (e.g. the mucosal addressin MAdCAM (e.g., MAdCAM-1), fibronectin).

Papain digestion of antibodies produces two identical antigen binding fragments, called "Fab" fragments, each with a single antigen binding site, and a residual "Fc" fragment, whose name reflects its ability to crystallize readily. Pepsin treatment yields an F(ab')$_2$ fragment that has two antigen binding sites and is still capable of cross-linking antigen.

"Fv" is an antibody fragment which consists of a dimer of one heavy chain variable domain and one light chain variable domain in non-covalent association.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments which have hinge cysteines between them. Other chemical couplings of antibody fragments are also known.

"Single-chain Fv" or "scFv" antibody fragments comprise the $V_H$ and $V_L$ domains of antibody, wherein these domains are present in a single polypeptide chain. In one aspect, the Fv polypeptide further comprises a polypeptide linker between the $V_H$ and $V_L$ domains which enables the scFv to form the desired structure for antigen binding. For a review of scFv see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen binding sites, which fragments comprise a variable heavy domain ($V_H$) connected to a variable light domain ($V_L$) in the same polypeptide chain ($V_H$-$V_L$). By using a linker that is too short to allow pairing between the two domains on the same chain, the domains are forced to pair with the complementary domains of another chain and create two antigen binding sites. Diabodies are described more fully in, for example, EP 404,097; WO 93/11161; and Hollinger et al., *Proc. Natl. Acad. Sci. USA*, 90:6444-6448 (1993).

A "full length antibody" is one which comprises an antigen binding variable region as well as a light chain constant domain ($C_L$) and heavy chain constant domains, $C_{H1}$, $C_{H2}$ and $C_{H3}$. The constant domains may be native sequence constant domains (e.g. human native sequence constant domains) or amino acid sequence variants thereof. In one aspect, the full length antibody has one or more effector functions.

An "amino acid sequence variant" antibody herein is an antibody with an amino acid sequence which differs from a main species antibody. Ordinarily, amino acid sequence variants will possess at least about 70%, at least about 80%, at least about 85%, at least about 90%, or at least about 95% homology with the main species antibody. The amino acid sequence variants possess substitutions, deletions, and/or additions at certain positions within or adjacent to the amino acid sequence of the main species antibody, but retain antigen binding activity. Variations in sequence of the constant regions of the antibody will have less effect on the antigen binding activity than variations in the variable regions. In the variable regions, amino acid sequence variants will be at least about 90% homologous, at least about 95% homologous, at least about 97% homologous, at least about 98% homologous, or at least about 99% homologous with the main species antibody.

"Homology" is defined as the percentage of residues in the amino acid sequence variant that are identical after aligning the sequences and introducing gaps, if necessary, to achieve the maximum percent homology. Methods and computer programs for the alignment are well known in the art.

A "therapeutic monoclonal antibody" is an antibody used for therapy of a human subject. Therapeutic monoclonal antibodies disclosed herein include anti-α4β7 antibodies.

Depending on the amino acid sequence of the constant domain of their heavy chains, full length antibodies can be assigned to different "classes". There are five major classes of full length antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

The "light chains" of antibodies from any vertebrate species can be assigned to one of two clearly distinct types, called kappa (κ) and lambda (λ), based on the amino acid sequences of their constant domains.

The terms "Fc receptor" or "FcR" are used to describe a receptor that binds to the Fc region of an antibody. In one aspect, the FcR is a native sequence human FcR. In another aspect, the FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (See review in M. Daeron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:33-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and for regulating the persistence of immunoglobulin G (IgG) and albumin in the serum (reviewed by Rath et al., *J. Clin. Immunol.* 33 Suppl 1:S9-17 (2013)).

The term "hypervariable region" when used herein refers to the amino acid residues of an antibody which are responsible for antigen binding and are found in the "variable domain" of each chain. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined. The hypervariable region or the CDRs thereof can be transferred from one antibody chain to another or to another protein to confer antigen binding specificity to the resulting (composite) antibody or binding protein.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

An "affinity matured" antibody is one with one or more alterations in one or more hypervariable regions thereof which result an improvement in the affinity of the antibody for antigen, compared to a parent antibody which does not possess those alteration(s). In one aspect, affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7): 3310-9 (1995); and Hawkins et al., *J. Mol. Biol.* 226:889-896 (1992).

An "isolated" antibody is one which has been identified and separated and/or recovered from a component of its natural environment. In certain embodiments, the antibody will be purified (1) to greater than 95% by weight of protein as determined by the Lowry method, and alternatively, more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

"Treatment" refers to both therapeutic treatment and prophylactic or preventative measures. Treatment refers to any type of measure that imparts a benefit to a subject or a patient afflicted with a disease, including improvement in the condition of the subject or patient (e.g., in one or more symptoms). Treatment may include any drug, drug product, method, procedure, lifestyle change, or other adjustment introduced in an attempt to effect a change in a particular aspect of a subject's health (i.e., directed to a particular disease, disorder, or condition). Those in need of treatment include those already with the disease as well as those in which the disease or its recurrence is to be prevented. Hence, the patient to be treated herein may have been diagnosed as having the disease or may be predisposed or susceptible to the disease. The terms "patient," "individual" and "subject" are used interchangeably herein.

As used herein, the term "a therapeutically effective amount" means an amount of the composition comprising the therapeutic agent that will affect a treatment of the subject as defined above. In some embodiments, a therapeutically effective amount improves the condition or delays the onset or progress of the condition of a subject without causing a significant side-effect or adverse event.

As used herein, "a healthy subject" means a subject that has not been diagnosed with PSC and/or does not exhibit any detectable symptoms associated with PSC.

The antibody which is formulated is substantially pure and desirably substantially homogeneous (i.e. free from contaminating proteins etc). "Substantially pure" antibody means a composition comprising at least about 90% antibody by weight, based on total weight of the protein in the composition, at least about 95% or 97% by weight. "Substantially homogeneous" antibody means a composition comprising protein wherein at least about 99% by weight of protein is specific antibody, e.g., anti-α4β7 antibody, based on total weight of the protein.

Treatment of PSC with Anti-α4β7 Antibodies

In one aspect, the invention relates to a method of treating PSC in a subject comprising administering to the subject an anti-α4β7 antibody described herein in an amount effective to treat PSC, e.g., in humans. The human subject may be an adult (e.g., 18 years or older), an adolescent, or a child. A patient suffering from PSC who can benefit from anti-α4β7 integrin antibody therapy can have abnormal liver function tests. For example, the patient can have an abnormal alkaline phosphatase test. In a PSC patient who can benefit from anti-α4β7 integrin antibody therapy, the alkaline phosphatase level can be greater than the upper limit of normal (ULN), e.g. 1.5 times ULN, 1.6 times ULN, 2 times ULN, 2.5 times ULN, 3 times ULN, 4 times ULN, or a range of 1.5 to 10 times ULN or a range of 3 to 12 times ULN. Other abnormal liver function tests which can be exhibited by a patient suffering from PSC include a test selected from the group consisting of alanine transaminase, γ-Glutamyl transpeptidase, aspartate transaminase, and total bilirubin. In some embodiments, the method relates to treating a PSC patient with an anti-α4β7 integrin antibody if the patient has an abnormal liver function test. In some embodiments, the method relates to treating a PSC patient with an anti-α4β7 integrin antibody if the patient has an abnormal alkaline phosphatase test. In some embodiments, the patient has elevated ALP that is not attributable to a hepatic or nonhepatic cause. In a further embodiment, the PSC patient can have liver fibrosis or IBD. The IBD can be ulcerative colitis, Crohn's disease or indeterminate, undifferentiated or unclassified IBD (IBDU). A patient suffering from PSC who can benefit from anti-α4β7 integrin antibody therapy can have abnormal liver stiffness. In some embodiments, the method relates to treating a PSC patient with an anti-α4β7 integrin antibody if the patient has a liver stiffness TE score of ≤20 kPa, ≤18 kPa, ≤16 kPa, ≤15 kPa, ≤14 kPa, ≤13 kPa. In an embodiment, a PSC patient is treated with an anti-α4β7 antibody if the liver stiffness TE score is ≤14.3 kPa. In some embodiments, the patient does not have elevated serum IgG4, e.g., at least 2 times its ULN or the IgG4/IgG1 ratio is above 0.24.

A pharmaceutical composition comprising an anti-α4β7 antibody can be used as described herein for treating PSC in a subject suffering therefrom. Typical PSC related clinical outcomes include, for example, progression to cirrhosis, liver failure, death and liver transplantation. PSC related clinical complications include, for example, ascites, hepatic encephalopathy, development of varices, jaundice, variceal bleeding, cholangiocarcinoma, hepatocellular carcinoma, evidence of cirrhosis, and colorectal cancer. The method and pharmaceutical compositions described herein can improve clinical outcome and/or clinical complications of PSC.

An effective amount of an anti-α4β7 antibody of the present invention is administered to an individual, e.g. a subject, in need thereof (e.g., a mammal, such as a human or other primate) in order to treat PSC. An effective amount of an anti-α4β7 antibody may be an amount sufficient to reduce, delay or prevent progression of PSC-related clinical complications, liver failure and/or death. For example, the effective amount of anti-α4β7 antibody can be an amount that is sufficient to maintain (e.g., prevent worsening), improve or normalize a clinical disease assessment score, or to maintain, reduce or normalize the level of a marker of liver function and/or pathology in the individual. In some aspects, the amount of anti-α4β7 antibody that is administered is sufficient to maintain, improve an Ishak fibrosis staging score, an amount sufficient to maintain, reduce or normalize serum alkaline phosphatase (ALP), an amount sufficient to maintain, improve Ishak necroinflammatory grading score, an amount sufficient to maintain, improve or normalize Amsterdam Cholestatic Complaints Score (ACCS), an amount sufficient to maintain, improve or normalize 5-D itch scale, an amount sufficient to maintain, improve or normalize the time to progression to cirrhosis by transient elastography (TE) assessed using FibroScan®, an amount sufficient to maintain, improve or normalize the time to PSC-related clinical outcomes or clinical complications, an amount sufficient to maintain, improve or normalize a subject's collagen proportional area (CPA, e.g., as assessed by histology), an amount sufficient to maintain, improve or normalize Enhanced Liver Fibrosis (ELF) score (e.g., as assessed by an algorithm using tests for serum concentrations of procollagen-III aminoterminal propeptide, tissue inhibitor of matrix metalloproteinase-1 and hyaluronic acid), an amount sufficient to maintain, improve or normalize liver stiffness score by Transient Elastography, an amount sufficient to maintain, improve or normalize liver stiffness score by Magnetic Resonance Elastography (MRE), an amount sufficient to maintain, improve or normalize Mayo PSC risk score, or any combination thereof.

Certain markers can be used as metrics to administer an effective amount of anti-α4β7 antibody. For example, in some aspects an amount of anti-α4β7 antibody that is sufficient to maintain, reduce or normalize a subject's serum alanine aminotransferase (ALT), aspartate aminotransferase (AST), gamma-glutamyl transpeptidase (GGT), bilirubin, vascular adhesion protein-1 (VAP-1), or any combination thereof, is administered. Alternatively or in addition, an effective amount of anti-α4β7 antibody may be an amount sufficient to maintain, improve or normalize a subject's platelet ratio index (APRI) or Fibrosis 4 (FIB-4) score.

In one embodiment, the invention relates to a method of treating PSC in a subject comprising administering to a subject an anti-α4β7 antibody described herein in an amount effective to reduce serum alkaline phosphatase (ALP) by at least about 20%, at least about 25%, at least about 30%, at least about 35%, at least about 40%, or at least about 45%. An effective amount of anti-α4β7 antibody may be an amount sufficient to normalize serum ALP in a subject. An effective amount of anti-α4β7 antibody may be an amount sufficient to reduce serum ALP in a subject to less than the Upper Limit of Normal (ULN). Reference range in human adults is 40-125 IU/L (VITROS® AnalyzerP, Ortho Clinical Diagnostics, Rochester, NY) or about 40 to about 150 IU/L (other methods). Less than ULN would be less than 200 IU/L, less than 175 IU/L, less than 150 IU/L, less than 145 IU/L, less than 140 IU/L, less than 135 IU/L, less than 130 IU/L or less than 125 IU/L.

In one embodiment, the invention relates to a method of treating PSC in a subject comprising administering to a subject an anti-α4β7 antibody described herein in an amount effective to improve the subject's Ishak necroinflammatory grading score by at least 1 or more points (e.g, 1, 2, 3, 4 points). In another embodiment, the invention relates to a method of treating PSC in a subject comprising administering to a subject an anti-α4β7 antibody described herein in an amount effective to prevent worsening of the subject's Ishak necroinflammatory grading score.

In other embodiments, an effective amount of anti-α4β7 antibody may be an amount sufficient to improve the 5-D itch score or the Amsterdam Cholestatic Complaints Score (ACCS) in a subject.

An endpoint such as no worsening of fibrosis, utilizes histology with Ishak fibrosis staging as a measure of structural and architectural alterations. PSC studies, both retrospective and prospective indicate that about ~50% of PSC patients will experience progression of fibrosis over 2 years. To date histology, via a liver biopsy, has been used to assess the progression of various liver diseases and has been included in clinical trials assessing the efficacy of new therapeutic agents. The scoring system proposed by Ishak has gained the most attention as it incorporates concepts relating to the pathogenesis of liver damage (inflammation and fibrosis), provides a wide range of possible assessment scores, and is also one of the few histology scoring systems to be shown to have prognostic value to long-term clinical outcomes.

Reductions or normalization of ALP levels have been demonstrated as a prognosis factor in PSC, being associated with increased overall survival times, increased liver transplant-free survival, and also reduced risk of cholangiocarcinoma.

Liver stiffness can be indicative of the extent of fibrosis in the liver. Healthy liver is soft or elastic, while fibrotic liver or a tumor in soft tissue, such as liver, is stiff. Noninvasive imaging techniques can measure the elastic properties of soft tissue such as liver. Ultrasound and magnetic resonance are two modalities for measuring elasticity of soft tissue. Transient elastography, e.g., using FIBROSCAN® Vibration Controlled Transient Elastography (by echosens France, is an ultrasound method and has demonstrated that liver stiffness progression is associated with clinical outcomes in PSC. Therefore, 'progression to cirrhosis' as assessed by FIBROSCAN® is another alternative assessment for determining an effective amount. Magnetic Resonance Elastography (MRE) is a non-invasive imaging technique that may be used in subjects to assess liver stiffness to evaluate the impact of anti-α4β7 antibodies on inflammation and fibrosis. Other modalities include strain imaging, acoustic shear wave imaging and supersonic shear imaging.

In one embodiment, an assessment of the extent of liver fibrosis is measured using transient elastography. In another embodiment, an assessment of the extent of liver fibrosis is measured using magnetic resonance elastography. An effective amount of anti-α4β7 antibody can be an amount sufficient to maintain, improve or normalize the elasticity of the liver. In some embodiments, an effective amount of anti-α4β7 antibody reduces liver stiffness at least 10%, at least 20%, at least 30%, at least 40%, at least 50% or at least 60% from the amount of stiffness prior to treatment or since the prior dose of anti-α4β7 antibody.

In other embodiments, an effective amount of an anti-α4β7 antibody can be an amount sufficient to reduce morbidity or mortality of PSC. For example, an effective amount of an anti-α4β7 antibody can be an amount sufficient to provide one or more of the following effects: a reduction of or limit of the number of episodes of cholangitis, an increase in the period of time between episodes of cholangitis, a reduction in the number of strictures, a reduction of the likelihood of development of portal hypertension or complications from hypertension, a reduction in hepatic osteodystrophy, such as a maintenance of bone density, and/or an improvement in pruritus. In some embodiments, an effective amount of an anti-α4β7 antibody can be an amount sufficient to reduce biliary disease burden, e.g. as measured on a magnetic resonance cholangiopancreatogram.

For therapy, an effective amount of anti-α4β7 antibody will be sufficient to achieve the desired therapeutic (including prophylactic) effect (such as an amount sufficient to reduce or prevent α4β7 integrin-mediated binding and/or signaling, thereby inhibiting leukocyte adhesion and infiltration and/or associated cellular responses in the liver and/or the bile ducts). An effective amount of an anti-α4β7 antibody, e.g., an effective titer sufficient to maintain saturation, e.g., neutralization, of α4β7 integrin, can treat PSC.

An effective dose can be administered in a unit dose or multiple doses. The dosage can be determined by methods known in the art and can be dependent, for example, upon the individual's age, sensitivity, tolerance and overall well-being. A clinician or pharmacist of ordinary skill can determine appropriate dosing using the guidance provided herein and conventional methods. For example, the levels of a marker in the individual being treated can be measured (e.g., ALP) and dosing can be adjusted to achieve the desired reduction or normalization of the level of the marker. Examples of modes of administration include topical routes such as nasal or inhalational or transdermal administration, enteral routes, such as through a feeding tube or suppository, and parenteral routes, such as intravenous, intramuscular, subcutaneous, intraarterial, intraperitoneal, or intravitreal administration. Suitable dosages for antibodies can be from about 0.1 mg/kg body weight to about 10.0 mg/kg body weight per treatment, for example about 2 mg/kg to about 7 mg/kg, about 3 mg/kg to about 6 mg/kg, or about 3.5 to about 5 mg/kg. In particular embodiments, the dose administered is about 0.3 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg. A dose of anti-α4β7 antibody can be in a range of 280 to 320 mg or antibody or consist of 300 mg of antibody. A dose of anti-α4β7 antibody can be in a range of 45 to 60 mg of antibody or consist of 54 mg of antibody. A dose of anti-α4β7 antibody can be in a range of 95 to 115 mg of antibody or consist of 108 mg of antibody. A dose of anti-α4β7 antibody can be in a range of 150 to 175 mg of antibody or consist of 160 or 165 mg of antibody. A dose of anti-α4β7 antibody can consist of a double dose, e.g., 600 mg, 480 mg or 216 mg of antibody.

In some embodiments, a formulation or composition comprising the anti-α4β7 antibody can comprise a mixture of a non-reducing sugar, e.g., sucrose, an anti-α4β7 antibody and at least one free amino acid, and the molar ratio of non-reducing sugar to anti-α4β7 antibody (mole:mole) is greater than 600:1 and the ratio of free amino acid to anti-α4β7 antibody (mole:mole) is greater than 250:1. In liquid form, the liquid formulation or composition can comprise at least about 40 mg/ml to about 80 mg/ml anti-α4β7 antibody, at least about 50-175 mM of one or more amino acids, and at least about 6% to at least about 10% (w/v) sugar. In another embodiment, the formulation or composition is a lyophilized formulation comprising a non-reducing sugar, an anti-α4β7 antibody, histidine, arginine and polysorbate 80, wherein the molar ratio of non-reducing sugar to anti-α4β7 antibody (mole:mole) in the formulation is greater than 600:1 and the molar ratio of arginine to anti-α4β7 antibody (mole:mole) in the formulation is greater than 250:1. In liquid form, e.g., thawed, prior to lyophilization or after reconstitution from a dry state, a formulation can comprise 60 mg/mL anti-α4β7 antibody, 50 mM histidine, 125 mM arginine, 10% sucrose, 0.06% polysorbate 80, pH 6.3.

In other embodiments, a liquid formulation or composition comprising the anti-α4β7 antibody can comprise a mixture of anti-α4β7 antibody, citrate, histidine, arginine and polysorbate 80. In other embodiments, a stable liquid pharmaceutical formulation for use in the treatment can comprise anti-α4β7 antibody, citrate, histidine, arginine and polysorbate 80. A liquid formulation or composition of anti-α4β7 antibody can have an anti-α4β7 antibody concentration of greater than 100 mg/ml, such as 120 to 180 mg/ml, 150 to 175 mg/ml or about 160 mg/ml (+/−5%). In an embodiment, the formulation or composition comprises at least about 140 mg/ml or about 150 mg/ml to about 170 mg/ml, for example, about 160 mg/ml of an anti-α4β7 antibody, a buffering agent (e.g., histidine), at least about 5 mM citrate to no more than 30 mM citrate and a free amino acid (e.g., arginine). In another embodiment, the formulation or composition comprises at least about 160 mg/ml of an anti-α4β7 antibody, a buffering agent (e.g., histidine), at least about 5 mM citrate, polysorbate 80 (e.g. 0.2% PS80), and a free amino acid (e.g., arginine). In an embodiment, a liquid formulation or composition can comprise 160 mg/mL anti-α4β7 antibody, 125 mM arginine, 50 mM histidine, 25 mM citrate, and 0.2% PS80 (Protein Molar Ratio 1.5). Formulations of anti-α4β7 antibody are described in PCT publications WO2012151248 and WO2012151247, the entire contents of which are incorporated by this reference.

The final dosage form, e.g., after dilution of an anti-α4β7 antibody, e.g., reconstituted from a lyophilized formulation (e.g., then diluted in a saline, Ringer's solution or 5% dextrose infusion system) of the anti-α4β7 antibody can be about 0.5 mg/ml to about 5 mg/ml for administration. The final dosage form may be at a concentration of between about 1.0 mg/ml to about 1.4 mg/ml, about 1.0 mg/ml to about 1.3 mg/ml, about 1.0 mg/ml to about 1.2 mg/ml, about 1.0 to about 1.1 mg/ml, about 1.1 mg/ml to about 1.4 mg/ml, about 1.1 mg/ml to about 1.3 mg/ml, about 1.1 mg/ml to about 1.2 mg/ml, about 1.2 mg/ml to about 1.4 mg/ml, about 1.2 mg/ml to about 1.3 mg/ml, or about 1.3 mg/ml to about 1.4 mg/ml. The final dosage form may be at a concentration of about 0.6 mg/ml, 0.8 mg/ml, 1.0 mg/ml, 1.1 mg/ml, about 1.2 mg/ml, about 1.3 mg/ml, about 1.4 mg/ml, about 1.5 mg/ml, about 1.6 mg/ml, about 1.8 mg/ml or about 2.0 mg/ml. In one embodiment, the total dose is 180 mg. In another embodiment, the total dose is 300 mg. A 300 mg anti-α4β7 antibody dose can be diluted into a larger volume, e.g., 250 ml, saline, Ringer's solution or 5% dextrose solution for administration, e.g., intravenous administration.

In some aspects, the dosing regimen has two phases, an induction phase and a maintenance phase. In the induction phase, the antibody or antigen-binding fragment thereof is administered in a way that quickly provides an effective amount of the antibody or antigen binding fragment thereof suitable for certain purposes, such as inducing immune tolerance to the antibody or antigen-binding fragment thereof or for inducing a clinical response and ameliorating primary sclerosing cholangitis symptoms. A patient can be administered an induction phase treatment when first being treated by an anti-α4β7 antibody, when being treated after a long absence from therapy, e.g., more than three months, more than four months, more than six months, more than nine months, more than one year, more than eighteen months or more than two years since anti-α4β7 antibody therapy or during maintenance phase of anti-α4β7 antibody therapy if there has been a return of primary sclerosing cholangitis symptoms, e.g., a relapse from remission of disease, e.g., an increase in ALP measurements (e.g., >ULN, e.g., >125 IU/L, >130 IU/L, >135 IU/L, >140 IU/L or >145 IU/L) or an ALP measurement at least 1.6 times ULN. In some embodiments, the induction phase regimen results in a higher mean trough serum concentration, e.g., the concentration just before the next dose, than the mean steady state trough serum concentration maintained during the maintenance regimen.

In the maintenance phase, the antibody or antigen-binding fragment thereof is administered in a way that continues the response achieved by induction therapy with a stable level of antibody or antigen-binding fragment thereof. A maintenance regimen can prevent return of symptoms or relapse of primary sclerosing cholangitis. A maintenance regimen can provide convenience to the patient, e.g., be a simple dosing regimen or require infrequent trips for treatment. In some embodiments, the maintenance regimen can include administration of the anti-α4β7 antibody or antigen-binding fragment thereof, e.g., in a formulation, composition, use and/or treatment method described herein, by a strategy selected from the group consisting of low dose, infrequent administration, self-administration and a combination any of the foregoing.

In one embodiment, e.g., during an induction phase of therapy, the dosing regimen provides an effective amount of an anti-α4β7 antibody or antigen-binding fragment in a formulation, composition, use and/or treatment method described herein for inducing remission of primary sclerosing cholangitis in a human patient. In some embodiments, the effective amount of the anti-α4β7 antibody is sufficient to achieve about 5 µg/ml to about 60 µg/ml, about 10 µg/ml to about 75 µg/ml, about 15 µg/ml to about 45 µg/ml, about 20 µg/ml to about 30 µg/ml, or about 25 µg/ml to about 35 µg/ml mean trough serum concentration of the anti-α4β7 antibody by the end of the induction phase. The duration of induction phase can be about three weeks, about four weeks, about five weeks, about six weeks, about seven weeks, about eight weeks, about ten weeks or about two to eight weeks of treatment, e.g., when the patient is beginning treatment with the anti-α4β7 antibody or has no anti-α4β7 antibody in circulation (e.g., after a long elapsed time (such as 6 months to two years) since the previous treatment. In some embodiments, the induction regimen can utilize a strategy selected from the group consisting of high dose, frequent administration, and a combination of high dose and frequent administration of the anti-α4β7 antibody or antigen-binding fragment thereof, e.g., in a formulation or composition described herein. Induction dosing can be once, or a plurality of more than one dose, e.g., at least two doses. During induction phase, a dose can be administered once per day, every other day, twice per week, once per week, once every ten days, once every two weeks or once every three weeks. In some embodiments, the induction doses are administered within the first two weeks of therapy with the anti-α4β7 antibody. In one embodiment, induction dosing can be once at initiation of treatment (day 0) and once at about two weeks after initiation of treatment. In another embodiment, the induction phase duration is six weeks. In another embodiment, the induction phase duration is six weeks and a plurality of induction doses are administered during the first two weeks.

In some embodiments, e.g., when initiating treatment of a patient with severe primary sclerosing cholangitis, the induction phase needs to have a longer duration than for patients with mild or moderate disease. In some embodiments, the induction phase for a patient with a severe disease can have a duration of at least 6 weeks, at least 8 weeks, at least 10 weeks, at least 12 weeks or at least 14 weeks. In one embodiment, an induction dosing regimen for a patient with a severe disease can include a dose at week 0 (initiation of treatment), a dose at week 2 and a dose at week 6. In another embodiment, an induction dosing regimen for a patient with a severe disease can comprise a dose every week for four weeks or a dose at week 0 (initiation of treatment), a dose at week 2 and a dose at week 4. In another embodiment, an induction dosing regimen for a patient with a severe disease can comprise a dose at week 0 (initiation of treatment), a dose at week 2, a dose at week 6 and a dose at week 10.

In one embodiment, e.g., during a maintenance phase of therapy, the dosing regimen maintains a mean steady state trough serum concentration, e.g., the plateau concentration just before the next dose, of about 5 to about 25 µg/mL, about 7 to about 20 µg/mL, about 5 to about 10 µg/mL, about 10 to about 20 µg/mL, about 15 to about 25 µg/mL, about 15 to about 40 µg/mL, about 20 to about 45 µg/mL or about 9 to about 13 µg/mL of anti-α4β7 antibody. In another embodiment, the dosing regimen e.g., during a maintenance phase of therapy, maintains a mean steady state trough serum concentration of about 10 to about 50 µg/mL, about 20 to about 30 µg/mL, about 20 to about 55 µg/mL, about 30 to about 45 µg/mL, about 45 to about 55 µg/mL or about 35 to about 40 µg/mL of anti-α4β7 antibody. In some embodiments, treatment with an effective amount of anti-α4β7 antibody maintains a mean serum trough concentration of anti-α4β7 antibody in a range of 20 to 100 µg/mL, 25 to 75 µg/mL or 30 to 60 µg/mL. The amount of anti-α4β7 antibody can be measured using an agent which specifically detects the antibody. For example, an anti-idiotypic antibody raised from the anti-α4β7 antibody can be used in assays, such as ELISA assays, to detect and measure the amount of anti-α4β7 antibody in serum.

The dose can be administered twice per week, once per week, once every 10 days, once every 2 weeks, once every 3 weeks, once every 4 weeks, once every month, once every 6 weeks, once every 8 weeks, once every 10 weeks or once every 4 to 12 weeks. A higher or more frequent dose, e.g., once or twice per week, once every 2 weeks, once every 3 weeks or once every 4 weeks, can be useful for inducing remission of active disease or for treating a new patient, e.g., for inducing tolerance to the anti-α4β7 antibody. A less frequent dose, e.g., once every 4 weeks, once every 5 weeks, once every 6 weeks, once every 8 weeks, once every 10 weeks or once every 4 to 12 weeks, can be useful for preventative therapy, e.g., to maintain remission of a patient with chronic disease. In one aspect, the treatment regimen is treatment at day 0, about week 2, about week 6 and every 4 or 8 weeks thereafter. In one embodiment, the maintenance regimen includes a dose of anti-α4β7 antibody every 4 weeks. In one embodiment, the maintenance regimen includes a dose of anti-α4β7 antibody every 8 weeks. In an embodiment, wherein a patient on a one dose every eight weeks maintenance regimen experiences a return of one or more disease symptoms, e.g., has a relapse, the dosing frequency can be increased, e.g., to once every 4 weeks.

The dose can be administered to the patient in about 20 minutes, about 25 minutes, about 30 minutes, about 35 minutes, or about 40 minutes, e.g., as a continuous infusion, e.g., intravenously. The dose can be self-administered, e.g., by self-injection, such as a subcutaneous injection.

The dosing regimen can be optimized to induce a clinical response and clinical remission in the primary sclerosing cholangitis of the patient. In some embodiments, the dosing regimen does not alter the ratio of CD4 to CD8 in cerebrospinal fluid of patients receiving treatment.

In some aspects, a durable clinical remission, for example, a clinical remission which is sustained through at least two, at least three, at least four visits with a caretaking physician within a six month or one year period after beginning treatment may be achieved with an optimized dosing regimen.

In some aspects, a durable clinical response, for example, a clinical response which is sustained for at least 6 months, at least 9 months, at least a year, at least 18 months after the start of treatment, may be achieved with an optimized dosing regimen.

In some embodiments, the dosing regimen for anti-α4β7 antibody therapy comprises an initial dose of anti-α4β7 antibody of 100 to 900 mg, 150 to 500 mg or 250 to 350 mg, one to four subsequent doses of 100 to 900 mg, 150 to 600 mg or 200 to 350 mg at about one to three week intervals within about one to ten weeks after the initial dose, and, thereafter (e.g., after the induction, initial higher doses), further subsequent doses of 40 to 500 mg or 50 to 350 mg at about two to twelve week intervals, e.g., in a maintenance phase regimen. In some embodiments, the anti-α4β7 antibody is vedolizumab. In some embodiments, all doses are administered intravenously. In some embodiments, all doses are administered subcutaneously. In some embodiments, the initial higher doses (i.e., induction phase) are administered intravenously and the subsequent lower, long interval doses (i.e., maintenance phase) are administered subcutaneously. In some embodiments, the doses for each administration are provided in one article of manufacture, e.g, a single vial or syringe. In other embodiments the doses are provided in more than one article of manufacture, e.g, two or three vials or syringes.

In one embodiment, the dosing regimen comprises an initial dose of 300 mg, a second subsequent dose of 300 mg about two weeks after the initial dose, a third subsequent dose of 300 mg at about six weeks after the initial dose, followed by a fourth and subsequent doses of 300 mg every four weeks or every eight weeks after the third subsequent dose. In some embodiments, the anti-α4β7 antibody is vedolizumab. In some embodiments, all doses are administered intravenously.

In one embodiment, the dosing regimen for anti-α4β7 antibody therapy comprises an initial dose of anti-α4β7 antibody of 300 mg, a second subsequent dose of 300 mg about two weeks after the initial dose, a third subsequent dose of 108 mg at about six weeks after the initial dose, followed by a fourth and subsequent doses of 108 mg every week, every two weeks, every three weeks, or every four weeks after the third subsequent dose. In some embodiments, the anti-α4β7 antibody is vedolizumab. In some embodiments, the induction doses are administered intravenously and the maintenance doses are administered subcutaneously.

In one embodiment, the dosing regimen for anti-α4β7 antibody therapy comprises an initial dose of anti-α4β7 antibody of 160 mg, a second subsequent dose of 160 mg about one week after the initial dose, a third subsequent dose of 160 mg at about two weeks after the initial dose, a fourth subsequent dose of 108 mg at about four weeks after the initial dose, followed by a fifth and subsequent doses of 108 mg every week, every two weeks, every three weeks, or every four weeks after the third subsequent dose. In some embodiments, the anti-α4β7 antibody is vedolizumab. In some embodiments, all doses are administered subcutaneously.

In some embodiments, the method of treatment, dose or dosing regimen reduces the likelihood that a patient will develop a HAHA response to the anti-α4β7 antibody. The development of HAHA, e.g., as measured by antibodies reactive to the anti-α4β7 antibody, e.g., antibodies in a patient serum sample, can increase the clearance of the anti-α4β7 antibody, e.g., reduce the serum concentration of the anti-α4β7 antibody, e.g., lowering the number of anti-α4β7 antibody bound to α4β7 integrin, thus making the treatment less effective. In some embodiments, to prevent HAHA, the patient can be treated with an induction regimen followed by a maintenance regimen. In some embodiments, there is no break between the induction regimen and the maintenance regimen. In some embodiments, the induction regimen comprises administering a plurality of doses of anti-α4β7 antibody to the patient. To prevent HAHA, the patient can be treated with a high initial dose, e.g., at least 1.5 mg/kg, at least 2 mg/kg, at least 2.5 mg/kg, at least 3 mg/kg, at least 5 mg/kg, at least 8 mg/kg, at least 10 mg/kg or about 2 to about 6 mg/kg, or frequent initial administrations, e.g., about once per week, about once every two weeks or about once every three weeks, of the standard dose when beginning therapy with an anti-α4β7 antibody. In some embodiments, the method of treatment maintains at least 30%, at least 40%, at least 50%, at least 60%, at least 70%, at least 80%, at least 90% or at least 95% of patients as HAHA-negative. In other embodiments, the method of treatment maintains patients as HAHA-negative for at least 6 weeks, at least 10 weeks at least 15 weeks, at least six months, at least 1 year, at least 2 years, or for the duration of therapy. In some embodiments, the patients, or at least 30%, at least 40%, at least 50% or at least 60% of patients who develop HAHA maintain a low titer, e.g., ≤125, of anti-α4β7 antibody. In an embodiment, the method of treatment maintains at least 70% of patients as HAHA-negative for at least 12 weeks after beginning therapy with an anti-α4β7 antibody. In an embodiment, the method of treatment maintains at least 80% of patients as with no more than two consecutive samples, e.g., samples from two consecutive visits, testing HAHA-positive after beginning therapy with an anti-α4β7 antibody.

The formulation, composition or dose may be administered to an individual (e.g., a human) alone or in conjunction with another agent. A formulation, composition or dose of the invention can be administered before, along with or subsequent to administration of the additional agent. In one embodiment, more than one formulation or therapeutic agent which inhibits the binding of α4β7 integrin to its ligands is administered. In such an embodiment, an agent, e.g., a monoclonal antibody, such as an anti-MAdCAM (e.g., anti-MAdCAM-1) or an anti-VCAM-1 monoclonal antibody can be administered. In another embodiment, the additional agent inhibits the binding of leukocytes to an endothelial ligand in a pathway different from the α4β7 pathway. Such an agent can inhibit the binding, e.g. of chemokine (C-C motif) receptor 9 (CCR9)-expressing lymphocytes to thymus expressed chemokine (TECK or CCL25) or an agent which prevents the binding of LFA-1 to intercellular adhesion molecule (ICAM). For example, an anti-TECK or anti-CCR9 antibody or a small molecule CCR9 inhibitor, such as inhibitors disclosed in PCT publication WO03/099773 or WO04/046092, or anti-ICAM-1 antibody or an oligonucleotide which prevents expression of ICAM, is administered in addition to a formulation, dose or composition of the present invention. In yet another embodiment, an additional active ingredient (e.g., an anti-inflammatory compound, such as sulfasalazine, azathioprine, 6-mercaptopurine, 5-aminosalicylic acid containing anti-inflammatories, another non-steroidal anti-inflammatory compound, a steroidal anti-inflammatory compound, or antibiotics commonly administered for control of IBD (e.g. ciprofloxacin, metronidazole), or another biologic agent (e.g. TNF alpha antagonists) can be administered in conjunction with a formulation, composition or dose of the present invention. In an embodiment, a bile analog, e.g., ursodeoxycholic acid, can be administered in conjunction with a formulation, composition or dose of the anti-α4β7 antibody.

In an embodiment, the dose of the co-administered medication can be decreased over time during the period of treatment by the formulation, composition or dose comprising the anti-α4β7 antibody. For example, a patient being treated with a steroid (e.g. prednisone, prednisolone) at the beginning, or prior to, treating with the anti-α4β7 antibody formulation, composition or dose would undergo a regimen of decreasing doses of steroid beginning as early as 6 weeks of treatment with the anti-α4β7 antibody formulation. The steroid dose will be reduced by about 25% within 4-8 weeks of initiating tapering, by 50% at about 8-12 weeks and 75% at about 12-16 weeks of tapering during treatment with the anti-α4β7 antibody formulation, composition or dose. In one aspect, by about 16-24 weeks of treatment with the anti-α4β7 antibody formulation, composition or dose, the steroid dose can be eliminated. In another example, a patient being treated with an anti-inflammatory compound, such as 6-mercaptopurine at the beginning, or prior to, treating with the anti-α4β7 antibody formulation, composition or dose would undergo a regimen of decreasing doses of anti-inflammatory compound similar to the tapering regimen for steroid dosing as noted above.

In one embodiment, the method comprises administering an effective amount of a pharmaceutical composition of an anti-α4β7 antibody to a patient, e.g., a patient suffering from PSC. The pharmaceutical composition may be administered when the patient is in a fed or fasted condition. If the pharmaceutical composition is in a solid, e.g., dry state, the process of administration can comprise a step of converting the pharmaceutical composition to a liquid state. In one aspect, a dry pharmaceutical composition can be reconstituted, e.g., by a liquid, such as water, isotonic saline or Ringer's solution, for use in injection, e.g. intravenous, intramuscular or subcutaneous injection. In an embodiment, if the pharmaceutical composition is supplied as a liquid, administration can proceed directly, e.g, for use in injection, e.g. intravenous, intramuscular or subcutaneous injection. In another aspect, a solid or dry pharmaceutical composition can be administered topically, e.g., in a patch, cream, aerosol or suppository.

In another aspect, the pharmaceutical composition of an anti-α4β7 antibody is a stable liquid formulation or composition, e.g., as a solution comprising anti-α4β7 antibody in a vial, cartridge, prefilled syringe or an autoinjector. The stable liquid formulation can comprise a high concentration of anti-α4β7 antibody, such as at least 60 mg/ml, at least 90 mg/ml, at least 120 mg/ml, at least 150 mg/ml, at least 155 mg/ml, at least 160 mg/ml, at least 165 mg/ml, 130 mg/ml to 180 mg/ml, 50 to 180 mg/ml, 60 to 70 mg/ml, 100 to 200 mg/ml, 145 to 175 mg/ml, or about 160 mg/ml. A stable liquid formulation or composition comprising anti-α4β7 antibody can be administered subcutaneously, intravenously, or intramuscularly. A stable liquid formulation comprising anti-α4β7 antibody can be self-administered.

In some embodiments, treatment with an anti-α4β7 antibody does not alter the ratio of CD4:CD8 lymphocytes. CD4:CD8 ratios can be measured in blood, lymph node aspirate, and cerebro-spinal fluid (CSF). The CSF CD4+: CD8+ lymphocyte ratios in healthy individuals are typically greater than or equal to about 1. (Svenningsson et al., *J. Neuroimmunol.* 1995; 63:39-46; Svenningsson et al., *Ann*

*Neurol.* 1993; 34:155-161). An immunomodulator can alter the CD4:CD8 ratio to less than 1.

In some embodiments, treatment with an anti-α4β7 antibody lengthens the amount of time to a PSC-related outcome or complication selected from the group consisting of death, liver failure, liver transplantation, ascites, hepatic encephalopathy, development of varices, jaundice, variceal bleeding, cholangiocarcinoma, hepatocellular carcinoma, evidence of cirrhosis, and colorectal cancer. In an embodiment, the treatment decreases the chance of progression to cirrhosis.

In one aspect, the invention relates to a method of treating PSC in a subject with an effective amount of an anti-α4β7 antibody, wherein said treatment does not cause an adverse event such as, for example, hepatotoxicity, progressive multifocal leukoencephalopathy (PML), cholangiocarcinoma, complications of portal hypertension (such as ascites, hepatic encephalopathy, development of varices, or jaundice), infusion-related reactions, infection, leucopenia, lymphopenia, colorectal cancer, acute respiratory failure, acute respiratory distress syndrome, Torsade de pointes, ventricular fibrillation, ventricular tachycardia, malignant hypertension, convulsive seizure, agranulocytosis, aplastic anemia, toxic epidermal necrolysis, Stevens-Johnson syndrome, hepatic necrosis, acute liver failure, anaphylactic shock, acute renal failure, pulmonary hypertension, pulmonary fibrosis, confirmed or suspected endotoxin shock, confirmed or suspected transmission of infectious agent by a medicinal product, neuroleptic malignant syndrome, malignant hyperthermia, spontaneous abortion, stillbirth, or fetal death. In some embodiments, a method of treating PSC in a subject with an effective amount of an anti-α4β7 antibody does not cause an adverse event such as ALT or AST elevated, e.g., in 2 consecutive measurements, >5 times their ULN or >5 times their baseline levels prior to treatment. In some embodiments, a method of treating PSC in a subject with an effective amount of an anti-α4β7 antibody does not cause an adverse event such as ALT or AST elevated >3 times their ULN or >3 times their baseline levels prior to treatment and the total bilirubin is >2 times its ULN or >2 times its baseline prior to treatment.

α4β7 Antibodies

Anti-α4β7 antibodies (anti-α4β7 integrin antibodies) suitable for use in the formulations, compositions, uses, methods and/or doses include antibodies from any desired source, such as fully human antibodies, murine antibodies, rabbit antibodies and the like, and any desired engineered antibodies, such as chimeric antibodies, humanized antibodies, and the like. Antigen-binding fragments of any of these types of antibodies, such as Fab, Fv, scFv, Fab' and F(ab')$_2$ fragments, are also suitable for use in the formulations, compositions, uses, methods and/or doses.

The anti-α4β7 antibody can bind to an epitope on the α4 chain (e.g., humanized MAb 21.6 (Bendig et al., U.S. Pat. No. 5,840,299), on the β7 chain (e.g., FIB504 or a humanized derivative (e.g., Fong et al., U.S. Pat. No. 7,528,236)), or to a combinatorial epitope formed by the association of the α4 chain with the β7 chain. In one aspect, the antibody binds a combinatorial epitope on the α4β7 complex, but does not bind an epitope on the α4 chain or the β7 chain unless the chains are in association with each other. The association of α4 integrin with β7 integrin can create a combinatorial epitope for example, by bringing into proximity residues present on both chains which together comprise the epitope or by conformationally exposing on one chain, e.g., the α4 integrin chain or the β7 integrin chain, an epitopic binding site that is inaccessible to antibody binding in the absence of the proper integrin partner or in the absence of integrin activation. In another aspect, the anti-α4β7 antibody binds both the α4 integrin chain and the β7 integrin chain, and thus, is specific for the α4β7 integrin complex. Such antibodies can bind α4β7 but not bind α4β1, and/or not bind α$_E$β7, for example. In another aspect, the anti-α4β7 antibody binds to the same or substantially the same epitope as the Act-1 antibody (Lazarovits, A. I. et al., *J. Immunol.*, 133(4): 1857-1862 (1984), Schweighoffer et al., *J. Immunol.*, 151(2): 717-729, 1993; Bednarczyk et al., *J. Biol. Chem.*, 269(11): 8348-8354, 1994). Murine ACT-1 Hybridoma cell line, which produces the murine Act-1 monoclonal antibody, was deposited under the provisions of the Budapest Treaty on Aug. 22, 2001, on behalf Millennium Pharmaceuticals, Inc., 40 Landsdowne Street, Cambridge, Mass. 02139, U.S.A., at the American Type Culture Collection, 10801 University Boulevard, Manassas, Va. 20110-2209, U.S.A., under Accession No. PTA-3663. In another aspect, the anti-α4β7 antibody is a human antibody or an α4β7 binding protein using the CDRs provided in U.S. Patent Application Publication No. 2010/0254975.

In one aspect, the anti-α4β7 antibody inhibits binding of α4β7 to one or more of its ligands (e.g. the mucosal addressin, e.g., MAdCAM (e.g., MAdCAM-1), fibronectin, and/or vascular addressin (VCAM)). Primate MAdCAMs are described in the PCT publication WO 96/24673, the entire teachings of which are incorporated herein by this reference. In another aspect, the anti-α4β7 antibody inhibits binding of α4β7 to MAdCAM (e.g., MAdCAM-1) and/or fibronectin without inhibiting the binding of VCAM.

In one aspect, the anti-α4β7 antibodies for use in the formulations, compositions, uses, doses and/or treatment methods described herein are humanized versions of the mouse Act-1 antibody. Suitable methods for preparing humanized antibodies are well-known in the art. Generally, the humanized anti-α4β7 antibody will contain a heavy chain that contains the 3 heavy chain complementarity determining regions (CDRs, CDR1, SEQ ID NO:8, CDR2, SEQ ID NO:9 and CDR3, SEQ ID NO:10) of the mouse Act-1 antibody and suitable human heavy chain framework regions; and also contain a light chain that contains the 3 light chain CDRs (CDR1, SEQ ID NO:11, CDR2, SEQ ID NO:12 and CDR3, SEQ ID NO:13) of the mouse Act-1 antibody and suitable human light chain framework regions. The humanized Act-1 antibody can contain any suitable human framework regions, including consensus framework regions, with or without amino acid substitutions. For example, one or more of the frame work amino acids can be replaced with another amino acid, such as the amino acid at the corresponding position in the mouse Act-1 antibody. The human constant region or portion thereof, if present, can be derived from the κ or λ light chains, and/or the γ (e.g., γ1, γ2, γ3, γ4), μ, α (e.g., α1, α2), δ or ε heavy chains of human antibodies, including allelic variants. A particular constant region (e.g., IgG1), variant or portions thereof can be selected in order to tailor effector function. For example, a mutated constant region (variant) can be incorporated into a fusion protein to minimize binding to Fc receptors and/or ability to fix complement (see e.g., Winter et al., GB 2,209,757 B; Morrison et al., WO 89/07142; Morgan et al., WO 94/29351, Dec. 22, 1994). Humanized versions of Act-1 antibody were described in PCT publications nos. WO98/06248 and WO07/61679, the entire teachings of each of which are incorporated herein by this reference.

In another aspect, the humanized anti-α4β7 antibody for use in the formulations, compositions, uses, doses and/or treatment methods comprises a heavy chain variable region comprising amino acids 20 to 140 of SEQ ID NO:2, and a light chain variable region comprising amino acids 20 to 131 of SEQ ID NO:4 or amino acids 21 to 132 of SEQ ID NO:5. If desired, a suitable human constant region(s) can be present. For example, the humanized anti-α4β7 antibody can comprise a heavy chain that comprises amino acids 20 to 470 of SEQ ID NO:2 and a light chain comprising amino acids 21 to 239 of SEQ ID NO:5. In another example, the humanized anti-α4β7 antibody can comprise a heavy chain that comprises amino acids 20 to 470 of SEQ ID NO:2 and a light chain comprising amino acids 20 to 238 of SEQ ID NO:4. The humanized anti-α4β7 antibody can be encoded by a heavy chain nucleic acid sequence of SEQ ID NO:1 and a light chain nucleic sequence of SEQ ID NO:3. The humanized light chain of vedolizumab (e.g., Chemical Abstract Service (CAS, American Chemical Society) Registry number 943609-66-3), with two mouse residues switched for human residues, is more human than the light chain of LDP-02. In addition, LDP-02 has the somewhat hydrophobic, flexible alanine 114 and a hydrophilic site (Aspartate 115) that is replaced in vedolizumab with the slightly hydrophilic hydroxyl-containing threonine 114 and hydrophobic, potentially inward facing valine 115 residue.

Further substitutions to the humanized anti-α4β7 antibody sequence can be, for example, mutations to the heavy and light chain framework regions, such as a mutation of isoleucine to valine on residue 2 of SEQ ID NO:14; a mutation of methionine to valine on residue 4 of SEQ ID NO:14; a mutation of alanine to glycine on residue 24 of SEQ ID NO:15; a mutation of arginine to lysine at residue 38 of SEQ ID NO:15; a mutation of alanine to arginine at residue 40 of SEQ ID NO:15; a mutation of methionine to isoleucine on residue 48 of SEQ ID NO:15; a mutation of isoleucine to leucine on residue 69 of SEQ ID NO:15; a mutation of arginine to valine on residue 71 of SEQ ID NO:15; a mutation of threonine to isoleucine on residue 73 of SEQ ID NO:15; or any combination thereof; and replacement of the heavy chain CDRs with the CDRs (CDR1, SEQ ID NO:8, CDR2, SEQ ID NO:9 and CDR3, SEQ ID NO:10) of the mouse Act-1 antibody; and replacement of the light chain CDRs with the light chain CDRs (CDR1, SEQ ID NO:11, CDR2, SEQ ID NO:12 and CDR3, SEQ ID NO:13) of the mouse Act-1 antibody.

In some embodiments, the anti-α4β7 antibody, e.g., a humanized anti-α4β7 antibody for use in the formulation, compositions, uses, doses and/or treatment methods comprises a heavy chain variable region that has about 95%, 96%, 97%, 98%, or 99% sequence identity to amino acids 20 to 140 of SEQ ID NO:2, and a light chain variable region that has about 95%, 96%, 97%, 98%, or 99% sequence identity to amino acids 20 to 131 of SEQ ID NO:4 or amino acids 21 to 132 of SEQ ID NO:5. Amino acid sequence identity can be determined using a suitable sequence alignment algorithm, such as the Lasergene system (DNASTAR, Inc., Madison, Wis.), using the default parameters. In an embodiment, the anti-α4β7 antibody for use in the formulation, compositions, uses, methods and/or doses is vedolizumab (CAS, American Chemical Society, Registry number 943609-66-3).

Other α4β7 antibodies may also be used in the formulations, compositions, uses, methods and/or dosing regimes described herein. For example, the α4β7 antibodies described in US 2010/0254975 (Amgen, Inc.) or the β7 antibodies described in WO2006026759 (Genentech, Inc.), incorporated by reference herein in its entirety, are suitable for use in the formulations, compositions, uses, doses and/or methods of treating primary sclerosing cholangitis in an individual.

The anti-α4β7 antibody can be produced by expression of nucleic acid sequences encoding each chain in living cells, e.g., cells in culture. A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an anti-α4β7 antibody in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3, NS0 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (1986); Cockett et al., *Bio/Technology* 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., *EMBO J.* 2:1791 (1983)), in which the antibody coding sequence may be ligated individually into the vector in frame with the lac Z coding region so that a fusion protein is produced; pIN vectors (Inouye & Inouye, *Nucleic Acids Res.* 13:3101-3109 (1985); Van Heeke & Schuster, *J. Biol. Chem.* 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, *Proc. Natl. Acad. Sci. USA* 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to Chinese hamster ovary (CHO), NS0, HeLa, VERY, baby hamster kidney (BHK), monkey kidney (COS), MDCK, 293, 3T3, WI38, human hepatocellular carcinoma cells (e.g., Hep G2), breast cancer cell lines such as, for example, BT483, Hs578T, HTB2, BT20 and T47D, and normal mammary gland cell line such as, for example, CRL7030 and Hs578Bst.

The glycosylation machinery of different cell types can produce antibodies with different glycosylation composition than in another cell type, or no glycosylation, as with bacterial cells. In one aspect, cell types for production of the anti-α4β7 antibody are mammalian cells, such as NS0 or CHO cells. In one aspect, the mammalian cells can comprise the deletion of an enzyme involved in cell metabolism and the exogenous gene of interest can be operably linked to a replacement enzyme, e.g., in a construct or vector for introduction into the cells, e.g., by transformation or transfection. The construct or vector with the exogenous gene confers to the cells which host the construct or vector a selection advantage to encourage production of the polypeptide encoded by the exogenous gene. In one embodiment, CHO cells are DG44 cells (Chasin and Urlaub (1980) *PNAS USA* 77:4216), comprising the deletion or inactivation of the dihydrofolate reductase gene. In another embodiment, CHO cells are CHO K1 cells comprising the deletion or inactivation of the glutamine synthase gene (see, e.g., U.S. Pat. No. 5,122,464 or 5,827,739).

In one aspect, the anti-α4β7 antibody is vedolizumab. Vedolizumab IV (also called MLN0002, ENTYVIO™ or KYNTELES™) is a humanized immunoglobulin (Ig) G1 mAb directed against the human lymphocyte integrin α4β7. The α4β7 integrin mediates lymphocyte trafficking to GI mucosa and gut-associated lymphoid tissue (GALT) through adhesive interaction with mucosal addressin cell adhesion molecule-1 (MAdCAM-1), which is expressed on the endothelium of mesenteric lymph nodes and GI mucosa. Vedolizumab binds the α4β7 integrin, antagonizes its adherence to MAdCAM-1 and as such, impairs the migration of gut homing leukocytes into GI mucosa. Without being bound by theory, it is believed that vedolizumab may be used as a therapeutic agent for PSC by blocking T-cell recruitment and the ongoing inflammatory process by binding to α4β7 integrin expressed on circulating lymphocytes.

Pharmaceutical Compositions

The anti-α4β7 antibody can be administered to the individual as part of a pharmaceutical or physiological composition for the treatment of primary sclerosing cholangitis (PSC). Such a composition can comprise an antibody or antigen-binding fragment thereof having binding specificity for α4β7 integrin as described herein, and a pharmaceutically or physiologically acceptable carrier. Pharmaceutical or physiological compositions for co-therapy can comprise an antibody or antigen-binding fragment having binding specificity for α4β7 integrin and one or more additional therapeutic agents. An antibody or antigen-binding fragment having binding specificity for α4β7 integrin function and an additional therapeutic agent can be components of separate compositions which can be mixed together prior to administration or administered separately. Formulation or composition will vary according to the route of administration selected (e.g., solution, emulsion, capsule). Suitable carriers can contain inert ingredients which do not interact with the antibody or antigen-binding fragment and/or additional therapeutic agent. Standard pharmaceutical formulation techniques can be employed, such as those described in Remington's Pharmaceutical Sciences, Mack Publishing Company, Easton, Pa. Suitable carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986). For inhalation, the agent can be solubilized and loaded into a suitable dispenser for administration (e.g., an atomizer, nebulizer or pressurized aerosol dispenser).

For example, the pharmaceutical composition may comprise a mixture of a non-reducing sugar, an anti-α4β7 antibody and at least one free amino acid, and the molar ratio of non-reducing sugar to anti-α4β7 antibody (mole:mole) is greater than 600:1. The pharmaceutical composition may be a liquid formulation or a dry formulation (e.g., lyophilized). The pharmaceutical composition can also contain a buffering agent. In some embodiments, the non-reducing sugar is mannitol, sorbitol, sucrose, trehalose, or any combination thereof. The free amino acid of the pharmaceutical composition may be histidine, alanine, arginine, glycine, glutamic acid, or any combination thereof. The pharmaceutical composition can comprise between about 50 mM to about 175 mM of free amino acid. The pharmaceutical composition can comprise between about 100 mM and about 175 mM of free amino acid. The ratio of free amino acid to antibody molar ratio can be at least 250:1. The pharmaceutical composition can also contain a surfactant. The surfactant can be polysorbate 20, polysorbate 80, a poloxamer, or any combination thereof.

The present invention will now be illustrated by the following Examples, which are not intended to be limiting in any way.

EXEMPLIFICATION

Example 1. A Randomized, Global, Double-Blind, Placebo-Controlled, Parallel-Group Study to Evaluate the Efficacy and Safety of Vedolizumab IV for the Treatment of Primary Sclerosing Cholangitis A phase 3 randomized, global, double-blind, parallel group, multicenter study will be done to assess the safety and efficacy of vedolizumab 300 mg IV infusion over a 106 week treatment period in non-end stage PSC subjects who also have inflammatory bowel disease (IBD). The study will include a 4-week Screening Period, a 106 week Treatment Period, and an 18-week Follow-up Period starting at Week 102 or the last dose of study drug for early withdrawal subjects. In addition, subjects will participate in a final safety visit at Week 120 and a follow-up safety survey at 6, 12, 18 and 24 months after the dose received at Week 102. Subjects who withdraw early from the study will be asked to undergo the end-of-treatment (EOT) assessments, including a liver biopsy (a liver biopsy will only be requested if they have completed ≥12 months treatment) and will begin the 24-month follow-up safety survey starting from their last dose date).

Approximately 228 subjects with non-endstage PSC and underlying IBD will be enrolled into the study. The subjects will be randomized into one of 2 treatment groups in a 2:1 ratio, stratified by concomitant use of ursodeoxycholic acid (UDCA) at baseline and participation in the magnetic resonance elastography (MRE) substudy. The total percentage of subjects on UDCA will be limited to approximately 25% and these subjects will be required to be at stable dose of up to 20 mg/kg UDCA for 8 weeks prior to the screening visit. If a subject needs to stop or change their UDCA dose, prior to study entry, this must occur 8 weeks prior to the Screening.

The treatment groups will be:

A: vedolizumab IV 300 mg at Day 1 (week 0) and Week 2; followed by vedolizumab IV 300 mg every 4 weeks (Q4W) starting from Week 6 (Weeks 6, 10, 14, 18, 22, 26, 30, 34, 38, 42, 46, 50, 54, 58, 62, 66, 70, 74, 78, 82, 86, 90, 94, 98, and 102).

B: placebo IV at Day 1 (week 0) and Week 2; followed by placebo Q4W starting from Week 6 (Weeks 6, 10, 14, 18, 22, 26, 30, 34, 38, 42, 46, 50, 54, 58, 62, 66, 70, 74, 78, 82, 86, 90, 94, 98, and 102).

An MRE substudy will be conducted at selected qualified sites, in a maximum of 114 subjects. This substudy will evaluate the effect of vedolizumab on fibrosis by assessing liver stiffness by MRE. Only subjects from the pre-selected sites will be included in this study; these subjects will undergo an MRE assessment at Screening, Week 54 and Week 106 or early termination (ET) visit, unless they have contraindications to the procedure. All MRE results will be evaluated by an independent central reviewer.

An interim analysis will be conducted when 50% of the maximum number of subjects (114 across both groups) have completed the 106 week treatment period or withdrawn from the study.

Pharmacogenomic analysis may be conducted to investigate the contribution of genetic variance on drug response, for example, its efficacy and safety.

The proposed study will also evaluate the effect of vedolizumab on inflammation, symptoms, biochemical markers, and other disease related clinical endpoints in non-endstage PSC subjects with underlying IBD. Pharmacokinetics (PK), pharmacodynamics (PD), and immunogenicity of vedolizumab in subjects with non-endstage PSC will be evaluated.

The impact of vedolizumab on patient reported outcomes includes quantifying health-related quality of life (HRQOL), using the Chronic Liver Disease Questionnaire (CLDQ) and EuroQOL (EQ-5D-3L), and work productivity, using the work productivity and activity impairment questionnaire (WPAI) in non-endstage PSC subjects.

For statistical analysis, the Full Analysis Set (FAS) will include all randomized subjects who receive at least 1 dose of study drug. Subjects in this set will be analyzed according to the treatment they were randomized to receive.

The Safety Analysis Set will include all subjects who receive at least 1 dose of study drug. Subjects in this set will be analyzed according to the treatment they actually received.

The PK and PD evaluable population is defined as all subjects who receive at least 1 dose of study drug and have sufficient blood sampling to allow for PK and PD evaluation.

The time to event endpoints will be analyzed using a Cox proportional hazard model with treatment group as a factor and stratified by randomization stratum.

Example 2. Identification of Patients Suffering from PSC

Background: A rare cholestatic liver disease and often concomitant with inflammatory bowel disease (IBD), primary sclerosing cholangitis (PSC) is broadly coded in non-Read code-based databases, e.g., UK Clinical Practice Research Datalink (CPRD GOLD). Within CPRD, Read codes for PSC and other forms of cholangitis are available. It is unknown if these conditions are appropriately recorded in the CPRD.

Objectives: To assess information in patients with PRC diagnosis in CPRD

Methods: Patients with a Read code for PSC in 1988-2013 but without a secondary sclerosing cholangitis diagnosis any time were eligible. We analyzed patient characteristics before PSC diagnosis among those with at least one year data before and after the first diagnosis.

Results: 371 patients (mean age 54±18, men 58.2%) were identified with PSC, of whom 9.7%, 3.2%, and 0.5% also had Read codes for cholangitis, sclerosing cholangitis, and other cholangitis diagnosis, respectively. 222 (59.8%) patients had at least one liver function test recorded. The number of patients tested and the percentage of patients with abnormal results were as follows: alkaline phosphatase (217, 87.1%), alanine transaminase (178, 55.6%), γ-Glutamyl transpeptidase (156, 87.2%), aspartate transaminase (69, 42.0%), and total bilirubin (208, 15.9%). IBD (43.7%, mostly ulcerative colitis 37.2%) was the most common medical history, followed by benign neoplasms (12.9%), cancers (5.9%, solid 5.1%), biliary cirrhosis (2.2%), and liver transplantation (1.4%).

Conclusions: A variety of indicators reflected a PSC diagnosis in CPRD GOLD. Research in assessing potential miscoding of PSC and developing PSC coding algorithms is under way.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Headings and subheadings, if any, are used for convenience only and do not limit the invention.

What is claimed is:

1. A method of preventing progression of primary sclerosing cholangitis (PSC) in a human patient in need thereof, said method comprising:

identifying a human patient who has a serum alkaline phosphatase (ALP) level at baseline of at least 1.6 times the upper limit of normal (ULN) and is being treated with up to 20 mg/kg ursodeoxycholic acid (UDCA), and administering 300 mg of an anti-α4β7 antibody to the human patient at weeks 0, 2, and 6 and every 4 weeks thereafter, wherein the human patient has stopped UDCA treatment by the start of the antibody treatment, such that the progression of PSC is prevented, wherein the serum ALP level of the human patient is reduced by at least 20% from the baseline, wherein the human patient has non-endstage PSC and inflammatory bowel disease (IBD), wherein prevention of progression of PSC is defined as prevention of a PSC-related outcome selected from the group consisting of progression to cirrhosis, liver failure, and liver transplantation, and wherein the anti-α4β7 antibody is a humanized antibody and has binding specificity for the α4β7 complex, wherein the antigen-binding region comprises the CDRs:

Light chain:   CDR1 SEQ ID NO: 11,
                   CDR2 SEQ ID NO: 12,
                   CDR3 SEQ ID NO: 13, Heavy chain:   CDR1 SEQ ID NO: 8,
                   CDR2 SEQ ID NO: 9, and
                   CDR3 SEQ ID NO: 10.

2. The method of claim 1, wherein the IBD is ulcerative colitis.

3. The method of claim 1, wherein the serum ALP level of the human patient is normalized.

4. The method of claim 1, wherein the serum ALP level is reduced by at least 35%.

5. The method of claim 1, wherein said method further comprises determining a level of gamma-Glutamyl transpeptidase of the human patient.

6. The method of claim 1, wherein said human patient has chronic cholestatic liver disease.

7. The method of claim 1, wherein said human patient's Ishak fibrosis staging score is improved, maintained or normalized or wherein the elasticity of the liver is maintained, improved or normalized.

8. The method of claim 1, wherein following administration of said anti-α4β7 antibody, said human patient's Amsterdam Cholestatic Complaints (ACCS) has improved, maintained or normalized, 5-D itch scale has improved, maintained or normalized, or said human patient has a liver stiffness TE score of less than or equal to 14.3 kPa, as assessed by Transient Elastrography.

9. The method of claim 1, wherein said anti-α4β7 antibody has a heavy chain variable region sequence comprising amino acid residues 20 to 140 of SEQ ID NO:2, and a light chain variable region comprising amino acids 20 to 131 of SEQ ID NO:4 or amino acids 21 to 132 of SEQ ID NO:5.

10. The method of claim 1, wherein said anti-α4β7 antibody is vedolizumab.

* * * * *